United States Patent [19]

Buckholz, Jr. et al.

[11] Patent Number: 5,372,834
[45] Date of Patent: Dec. 13, 1994

[54] TREATING A MEATY FLAVORED FOODSTUFF WITH A COMBINATION OF A SCLAREOLIDE AND ACONITIC OR GLUCONIC ACID

[75] Inventors: Lawrence L. Buckholz, Jr., Middletown; Lewis G. Scharpf, Fair Haven, both of N.J.

[73] Assignee: International Flavors & Fragances Inc., New York, N.Y.

[21] Appl. No.: 265,109

[22] Filed: Jun. 24, 1994

Related U.S. Application Data

[60] Division of Ser. No. 168,338, Dec. 17, 1993, which is a continuation of Ser. No. 981,522, Nov. 25, 1992, abandoned.

[51] Int. Cl.⁵ .............................................. A23L 1/231
[52] U.S. Cl. .................................... 426/536; 426/650
[58] Field of Search .............................. 426/536, 650

[56] References Cited

U.S. PATENT DOCUMENTS

| | | | |
|---|---|---|---|
| 3,578,465 | 5/1971 | van der Zijden et al. | 425/537 |
| 3,615,600 | 10/1971 | Tonsbeek | 426/548 |
| 4,258,072 | 3/1981 | Eguchi et al. | 426/537 |
| 4,917,913 | 4/1990 | Buckholz, Jr. et al. | 426/536 |

OTHER PUBLICATIONS

Sugita, "Recent Developments in Umami Research":, Chapter IV (pp. 63-79) of Developments in Food Flavors, Birch and Lindley, Elsevier Applied Science, 1986.

*Primary Examiner*—Joseph Golian
*Attorney, Agent, or Firm*—Arthur L. Liberman

[57] ABSTRACT

Described is the use of one or more of the acids: aconitic acid, gluconic acid and/or succinic acid taken alone or further together with sclareolide in augmenting or enhancing the organoleptic properites of foodstuffs particularly with respect to imparting a umami effect and/or imparting of mouthfeel and fullness to the flavor of foodstuffs in the absence of amino acids except sulfur-bearing amino acids, salts thereof, pyrrolidone carboxylic acid, salts thereof and nucleotides.

3 Claims, No Drawings

TREATING A MEATY FLAVORED FOODSTUFF WITH A COMBINATION OF A SCLAREOLIDE AND ACONITIC OR GLUCONIC ACID

This is a divisional of application Ser. No. 08/168,338 filed on Dec. 17, 1993, which, in turn, is a streamline continuation of U.S. Ser. No. 07/981,52 filed on Nov. 25, 1992, now abandoned.

BACKGROUND OF THE INVENTION

Our invention concerns the use of one or more of the acids: aconitic acid, gluconic acid and/or succinic acid taken alone or further together with sclareolide in acting as a monosodium glutamate total replacer and/or in augmenting or enhancing the organoleptic properties of foodstuffs particularly with respect to imparting an umami effect and/or imparting of mouthfeel and fullness to the flavor of foodstuffs.

The "umami" effect is defined as the taste of a group of amino acids and nucleotides such as glutamates, inosinates and guanylates. The "umami" effect is set forth in detail in "Developments In Food Flavors" edited by G. G. Birch and M. G. Lindley, Chapter IV, at pages 63–79 (author and title of Chapter IV: Yoshi-Hisa Sugita "Recent Developments in Umami Research") the disclosure of which is incorporated herein by reference.

The use of succinic acid in augmenting or enhancing the taste of foodstuffs is disclosed by Tonsbeek in U.S. Pat. No. 3,615,600 wherein an artificial flavoring mixture is described which can impart a meaty flavor to foods, and the mixtures contain an amino acid including glutamic acid, a nucleotide and critical amounts of succinic acid and a hydroxy carboxylic acid including lactic acid. However, the Tonsbeek reference does not teach the use of aconitic acid, gluconic acid and/or succinic acid taken alone (in the absence of amino acids except sulfur-bearing amino acids, salts thereof, pyrrolidone carboxylic acid, salts thereof and nucleotides) or further together with sclareolide in enhancing the organoleptic properties of foodstuffs; particularly as a monosodium glutamate replacer and/or as a provider of the "umami" effect in foodstuffs.

The use of sclareolide per se is described in U.S. Pat. No. 4,917,913 issued on Apr. 17, 1990 for augmenting or enhancing the organoleptic properties of foodstuffs whereby:

(i) richness and creaminess is added to low fat ice cream by admixing therewith the sclareolide;
(ii) the sweetness of foodstuffs and beverages sweetened with non-nutrative sweeteners, e.g., aspartame is enhanced by admixing with a non-nutrative sweetener prior to addition to the beverage or foodstuff, sclareolide; and
(iii) bitter nuances imparted by the use of potassium chloride and salt substitutes are substantially covered by means of admixing such salt substitutes with sclareolide.

However, U.S. Pat. No. 4,917,913 does not disclose the synergistic effect of sclareolide with aconitic acid, gluconic acid and/or succinic acid in enhancing the organoleptic properties of foodstuffs particularly with respect to providing an "umami" effect and/or providing a monosodium glutamate effect without the use of monosodium glutamate U.S. Pat. No. 4,258,072 issued on Mar. 24, 1981 discloses a mixed seasoning comprising 100 parts by weight monosodium glutamate; 0.05 to 25 parts by weight of a flavor inducing 5'-nucleotide; 5.0 to 38.0 parts by weight table salt; 0.1 to 0.87 parts by weight succinic acid and/or sodium succinate; and 0.5 to 10.0 parts by weight of at least one alkali salt of an organic acid selected from the group consisting of sodium fumarates, sodium citrate, sodium or calcium lactate, sodium maleate, sodium tartarate, sodium ascorbate and sodium aspartate.

However, U.S. Pat. No. 4,258,072 does not disclose the use of succinic acid in the absence of monosodium glutamate to provide an "umami" effect and/or to act as a monosodium glutamate replacer.

U.S. Pat. No. 3,578,465 issued on May 11, 1971 discloses an artificial flavoring composition comprising pyrrolidone carboxylic acid or a precursor thereof such as glutamine and succinic acid However, U.S. Pat. No. 3,578,465 does not disclose the use of succinic acid alone in the absence of such pyrrolidone carboxylic acid to provide an "umami" affect and/or to act as a monosodium glutamate replacer.

Nothing in the prior art describes the Use of one or more of the acids: aconitic acid, gluconic acid and/or succinic acid taken alone or further together with sclareolide in augmenting or enhancing the organoleptic properties of foodstuffs particularly with respect to imparting an "umami" effect and/or imparting of mouthfeel and fullness to the flavor of foodstuffs in the absence of amino acids except sulfur-bearing amino acids, salts thereof, pyrrolidone carboxylic acid, salts thereof and nucleotides particularly where the final effect is also to act as a monosodium glutamate replacer.

THE INVENTION

Our invention is drawn to the use of one or more the acids:

aconitic acid having the structure:

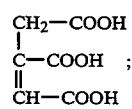

succinic acid having the structure:

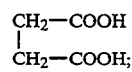

and/or gluconic acid having the structure:

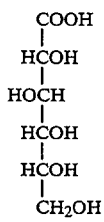

taken alone or taken further together with sclareolide having the structure:

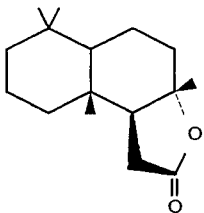

in augmenting or enhancing the organoleptic properties of foodstuffs particularly with respect to imparting an umami effect and/or imparting of mouthfeel and fullness to the flavor of foodstuffs in the absence of amino acids (except sulfur-bearing amino acids), salts thereof, pyrrolidone carboxylic acid, salts thereof, and nucleotides.

Our invention is also intended to cover mixtures per se of sclareolide having the structure:

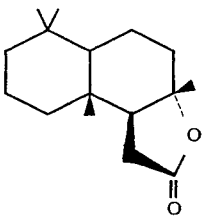

and succinic acid having the structure:

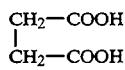

with the mole ratios of sclareolide:succinic acid rating from 1:99 down to 99:1; and with the preferred mole ratio of sclareolide: succinic acid being in the range of from about 0.1:1 up to 1:0.1.

Preferably, our invention covers the percentage of aconitic acid, succinic acid and/or gluconic acid on a finished basis in a foodstuff of from about 0.001% up to about 0.05%; and on a dry basis from about 0.15% up to about 1.5%.

The weight ratio of aconitic acid; gluconic acid and/or succinic acid to sclareolide (when the sclareolide is used) may vary from about 1:99 up to about 99:1 with a preferred weight ratio of about 0.5:1.5 up to about 1.5:0.5 of acid: sclareolide.

The mixtures of aconitic acid, gluconic acid and/or succinic acid taken alone or further together with sclareolide, may be used in various foodstuffs, preferably foodstuffs that have a meaty flavor such as chicken soup or biscuits or foodstuffs which require the "umami" effect as discussed in the Sugita Chapter IV "Recent Developments in Umami Research" which is part of the text "Developments In Food Flavors" by Birch and Lindley (Elsevier Applied Science), 1986, cited, supra.

With regard to the succinic acid useful in our invention, crystalline succinic acid is highly useful. Furthermore, succinic acid produced by means of fermentation is useful in practicing our invention. Thus, the succinic acid shown to be produced according to U.S. Pat. No. 5,143,833 issued on Sep. 1, 1992 and U.S. Pat. No. 5,143,834 issued on Sep. 1, 1992 are preferred forms of succinic acid so useful. By the same token, the calcium succinate and other succinic acid salts shown to be produced by U.S. Pat. Nos. 5,143,833 and 5,143,834 are preferred in practicing our invention.

The disclosures of said U.S. Pat. Nos. 5,143,833 issued on Sep. 1, 1992 and 5,143,834 issued on Sep. 1, 1992 are incorporated by reference herein.

Sulfur-containing amino acids useful in the practice of our invention are:

(i) cysteine;
(ii) cysteine hydrochloride;
(iii) taurine; and
(iv) cystine.

The following examples are given to illustrate embodiments of the invention as it is preferred to practice it. It will be understood that these examples are illustrative and the invention is not to be considered as restricted thereto except as indicated in the appended claims.

EXAMPLE I (A) Production of "Natural Chicken Flavor"

A chicken flavor is prepared by admixing the following materials:

| Ingredients | Parts by Weight |
| --- | --- |
| Butter oil | 240 |
| Chicken fat | 600 |
| Rosemary extract | 38 |
| Cooked chicken meat | 45 |
| Chicken broth (16% aqueous) | 50 |
| Egg yolk solids | 23.0 |

The resulting product is heated for a period of four hours at 62° C. and then cooled. The resulting mixture is used in Part (B).

(B) Production Of Thickened Natural Chicken Flavor

995 Parts of the product of Part (A) is admixed with five parts of silicon dioxide to produce a thickened natural chicken flavor. The resulting thickened natural chicken flavor is used in Part (C), infra.

(c) Production of "Chicken Flavor" For Use With Chicken Soup:

The following mixture is prepared:

| Ingredients | Parts by Weight |
| --- | --- |
| Cerelose 2001 (Produced by CPC International) | 204.0 |
| Chicken fat | 85.0 |
| Rosemary extract | 3.9 |
| Corn starch | 30.8 |
| Mor-Rex 1918 (Maltrin 100) (A mixture of malto dextrins manufactured by the National Starch Company (Division of Unilever) located at Bridgewater, New Jersey) | 204.0 |
| Onion Powder | 16.8 |
| Salt Flour | 203.0 |
| Tumeric Powder | 2.8 |
| Chicken Flavor of Part (B) | 200.0 |
| Natural chicken drippings | 47.6 |

The resulting product is admixed and heated for a period of three hours at 70° C. The resulting product is cooled and used for the chicken soup in Part (D), infra.

(D) Production of Chicken Soup

The following chicken soup formulations are prepared:

| Ingredients | Parts by Weight |
|---|---|
| Maltodextrin | 23 |
| Modified Corn Starch | 16 |
| Sodium Chloride | 20 |
| Dried Corn Syrup (24 Dextrose equivalents) | 12 |
| Chicken fat | 5 |
| Chicken Flavor of Part (C) | 21 |
| White Onion Powder | 2 |
| Parsley Flakes | 0.60 |
| Turmeric Powder | 0.40 |

9.0 Grams of the resulting product is added to 10 ounces of boiling water with stirring and stirring is maintained for a period of 0.5 hours. The resulting product is divided into five portions. Different acids are added to each portion as follows:

| Ingredient | On A Finished Basis | On A Dry Basis |
|---|---|---|
| Aconitic Acid | 0.0015% | 0.0465% |
| Adipic Acid | 0.03% | 0.97% |
| Gluconic Acid | 0.015% | 0.465% |
| Succinic Acid | 0.00675% | 0.22% |
| Tartaric Acid | 0.02% | 0.65% |

Each of the materials is discussed below:
1. Aconitic acid—extremely interesting; in addition to an overall enhancement of the flavor, a tremendous mouthfeel or fullness was imparted to the chicken broth.
2. Adipic Acid—little or no effect, slight saltiness or salinity was perceived with a slight metallic background.
3. Gluconic Acid—a definite lift in flavor and enhancement, also a fullness similar to the Aconitic Acid but not as intense. A slight umami type of effect.
4. Succinic Acid—a definite increase in overall flavor perception, definite enhancement. Very similar to an umami effect; tingling and brightness along the sides of the tongue with a slight metallic astringent aftertaste.
5. Tartaric Acid—little or no affect, slight sourness or tastiness with astringency.

EXAMPLE II (A) Production of "Natural Savory Flavor"

The following mixture was prepared:

| Ingredients | Parts by Weight |
|---|---|
| Citric Acid Anhydrous Crystalline | 5 |
| Mor-Rex 1918 (a mixture of Malto Dextrins manufactured by the National Starch Company of Bridgewater, New Jersey) | 300 |
| Onion Powder | 4 |
| Salt Flour | 400 |
| Beef extract | 150 |
| Sweet Whey | 129 |
| Malic Acid | 4 |
| Sclareolide | 5 |
| Lactic Acid | 3 |

The resulting mixture is divided into five parts, to each part a different acid is added as follows:

| 1. | Aconitic Acid | 7.5 Parts |
|---|---|---|
| 2. | Adipic Acid | 7.5 Parts |
| 3. | Gluconic Acid | 7.5 Parts |
| 4. | Succinic Acid | 7.5 Parts |
| 5. | Tartaric Acid | 7.5 Parts |

Although the sclareolide enhances the flavor of the resulting savory flavor product, only aconitic acid, gluconic acid and succinic acid cause an increased enhancement of the flavor over the sclareolide. The adipic acid and the tartaric acid have no effect. When the amount of sclareolide is increased to ten parts by weight, only the aconitic acid, the gluconic acid and the succinic acid have definite effects on increasing the flavor enhancement in a two-fold amount (e.g., a value of "8" on a scale of 1–10 from a value of "4" on a scale of 1–10). Furthermore, the succinic acid adds a definite umami effect.

EXAMPLE III (A) Production of "Natural Chicken Flavor"

A chicken flavor is prepared by admixing the following materials:

| Ingredients | Parts by Weight |
|---|---|
| Butter oil | 240 |
| Chicken fat | 600 |
| Rosemary extract | 38 |
| Cysteine hydrochloride | 5 |
| Cooked chicken meat | 45 |
| Chicken broth (16% aqueous) | 50 |
| Egg yolk solids | 23.0 |

The resulting product is heated for a period of flour hours at 62° C. and then cooled. The resulting mixture is used in Part (B).

(B) Production Of Thickened Natural Chicken Flavor

995 Parts of the product of Part (A) is admixed with five parts of silicon dioxide to produce a thickened natural chicken flavor. The resulting thickened natural chicken flavor is used in Part (C), infra.

(c) Production of "Chicken Flavor" For Use With Chicken Soup:

The following mixture is prepared:

| Ingredients | Parts by Weight |
|---|---|
| Cerelose 2001 (Produced by CPC International) | 204.0 |
| Chicken fat | 85.0 |
| Rosemary extract | 3.9 |
| Corn starch | 30.8 |
| Mor-Rex 1918 (Maltrin 100) (A mixture of malto dextrins manufactured by the National Starch Company (Division of Unilever) located at Bridgewater, New Jersey) | 204.0 |
| Onion Powder | 16.8 |
| Salt Flour | 203.0 |
| Tumeric Powder | 2.8 |
| Chicken Flavor of Part (B) | 200.0 |
| Natural chicken drippings | 47.6 |

The resulting product is admixed and heated for a period of three hours at 70° C. The resulting product is cooled and used for the chicken soup in Part (D), infra.

(D) Production of Chicken Soup

The following chicken soup formulations are prepared:

| Ingredients | Parts by Weight |
|---|---|
| Maltodextrin | 23 |
| Modified Corn Starch | 16 |
| Sodium Chloride | 20 |
| Dried Corn Syrup (24 Dextrose equivalents) | 12 |
| Chicken fat | 5 |
| Chicken Flavor of Part (C) | 21 |
| White Onion Powder | 2 |
| Parsley Flakes | 0.60 |
| Turmeric Powder | 0.40 |

9.0 Grams of the resulting product is added to 10 ounces of boiling water with stirring and stirring is maintained for a period of 0.5 hours. The resulting product is divided into five portions. Different acids are added to each portion as follows:

| Ingredient | On A Finished Basis | On A Dry Basis |
|---|---|---|
| Aconitic Acid | 0.0015% | 0.0465% |
| Adipic Acid | 0.03% | 0.97% |
| Gluconic Acid | 0.015% | 0.465% |
| Succinic Acid | 0.00675% | 0.22% |
| Tartaric Acid | 0.02% | 0.65% |

Each of the materials is discussed below:
1. Aconitic acid—extremely interesting; in addition to an overall enhancement of the flavor, a tremendous mouthfeel or fullness was imparted to the chicken broth.
2. Adipic Acid—little or no effect, slight saltiness or salinity was perceived with a slight metallic background.
3. Gluconic Acid—a definite lift in flavor and enhancement, also a fullness similar to the Aconitic Acid but not as intense. A slight umami type of effect.
4. Succinic Acid—a definite increase in overall flavor perception, definite enhancement. Very similar to an umami effect; tingling and brightness along the sides of the tongue with a slight metallic astringent aftertaste.
5. Tartaric Acid—little or no effect, slight sourness or tastiness with astringency.

What is claimed is:
1. A process for imparting, augmenting or enhancing the umami taste and mouthfeel of a meaty-flavored foodstuff consisting of adding no said foodstuff from 0.001% up to 0.05% of an umami taste and mouthfeel imparting, augmenting or enhancing quantity of a mixture of an acid selected from the group consisting of aconitic acid having the structure:

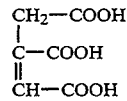

and gluconic acid having the structure:

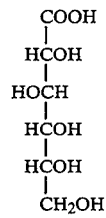

or a salt thereof and sclareolide having the structure:

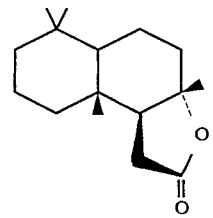

with the weight ratio of sclareolide:carboxylic acid or salt thereof being from 0.5:1.5 up to 1.5:0.5 in the absence of:
(i) amino acids except sulfur-bearing amino acids;
(ii) salts of amino acids except sulfur-bearing amino acids;
(iii) pyrollidone carboxylic acid;
(iv) sales of pyrollidone carboxylic acid; and
(v) nucleotides.

2. The process of claim 1 wherein the carboxylic acid is an aconitic acid having the structure:

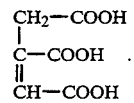

3. The process of claim 1 wherein the carboxylic acid is gluconic acid having the structure:

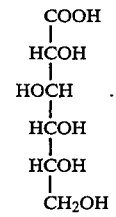

* * * * *